United States Patent [19]

Glenn et al.

[11] Patent Number: Plant 7,552

[45] Date of Patent: Jun. 11, 1991

[54] CHINESE ELM TREE NAMED 'EMER II'

[75] Inventors: Michael M. Glenn, Athens; John H. Barbour, Atlanta; Michael A. Dirr, Watkinsville, all of Ga.

[73] Assignee: Tree Introductions, Inc., Monroe, Ga.

[21] Appl. No.: 336,003

[22] Filed: Apr. 10, 1989

[51] Int. Cl.[5] ..... A01H 5/00

[52] U.S. Cl. ..... Plt./51

[58] Field of Search ..... Plt./51

[56] References Cited

U.S. PATENT DOCUMENTS

P.P. 5,554 9/1985 King ..... Plt. 51

*Primary Examiner*—James R. Feyrer

*Attorney, Agent, or Firm*—Klarquist, Sparkman, Campbell, Leigh & Whinston

[57] ABSTRACT

A new and distinct variety of *Ulmus parvifolia* of distinct vase-shaped growth habit which resembles an American Elm in ultimate mature tree shape. The tree is characterized in having exfoliating patchy bark in attractive patterns which cover exposed bark root portions, branches over one inch in diameter and the trunk which has distinctive butresses. The tree is exceedingly durable to extremes of weather, and is resistant to common Elm pests and diseases. The tree has a dense, strong upright branching habit, with narrow but very strong branch crotch angles, and numerous thin terminal twigs which produce a dense canopy of lustrous foliage. Leaves are densely borne at the terminals of the twigs to render a full, attractive shade tree.

3 Drawing Sheets

BACKGROUND OF THE INVENTION

The present invention relates to a new and distinct variety of Chinese or lacebark elm, *Ulmus parvifolia*, which is distinguished from all other named forms by virtue of the vase-shaped habit of growth which resembles the American Elm, *Ulmus americana*. The exfoliating patchy bark that develops on 1" to 2" diameter branches is present on the 3' diameter trunk, including the exposed surface roots. The tree was discovered in a cultivated area on the campus of the University of Georgia, Athens, Ga. and history relative to the tree is limited. The tree is 70 to 80 years old and has not suffered any visible branch or trunk damage. Ice storms are common in the Athens area and the Siberian Elm (*Ulmus pumila*); water oak (*Quercus nigra*); pecan, (*Carya illinoensis*), and other trees display extensive ice damage.

The tree has been asexually reproduced by rooting cuttings taken from the tree. Clones of the tree have been determined to be identical to the parent tree in all distinguishing characteristics of bark, leaves, stems and buds.

SUMMARY OF THE VARIETY

The instant variety of *Ulmus parvifolia* is most distinguished by virtue of its unique vase shape in maturity. The shape of this selection approaches or resembles the normal shape of the American Elm, *Ulmus americana*. The trunk of this tree is notably and attractively irregularly and attractively fluted with pronounced butresses which diminish with increased distance from the ground, and apparently add to the structural strength of the tree. This characteristic is conspicuously attractive and not usually seen in the species. The bark of the tree of this disclosure is also quite colorful and attractive, characteristically exfoliating on the tree from bark on exposed surface roots, along the trunk, to branches having more than 1 to 2 inch diameter. The tree may be compared to 'Emer I' in having vase-shaped rather than broad globe shape habit and by being taller than it is wide, by having leaves of a lighter green shade and by having lustrous, but leaves of less lustrous aspect, and by having the unique fluted trunk. Further, 'Emer II' asexually reproduces with more ease, and expresses greater vigor under the same growing conditions, with clones, once transplanted, growing 30 to 42 inches in a season. This combination of characteristics sets the claimed tree apart from the species, per se, as well as other market available varieties of Chinese Elm trees like 'A. Ross Central Park', 'Burgandy', 'Drake', 'Dynasty', 'Milliken' and both 'King's Choice' North and South.

BRIEF DESCRIPTION OF THE DRAWING

Sheet 1 of the drawing depicts in substantial side view, the parent specimen of the selection where mature size, unique vase shape, and the unusual fluted trunk can be seen, Sheet 2 of the drawing is a close-up view of the foliage, and terminal portions of stems taken from 'Emer II' (left side) and of 'Emer I' (right side); and, Sheet 3 of the drawing is a close-up view of the unusually attractive bark showing the blocky, puzzle-like pattern and coloration of bark and lenticels of this novel tree.

HORTICULTURAL AND BOTANICAL CHARACTERISTICS (The Royal Horticultural Colour Chart was used to describe colors where appropriate.)

The tree is upright-spreading, almost American elm-like outline, 70 feet high and 59 feet of spread (as shown in sheet 1 of the drawing). The trunk diameter is 3 feet and the circumference is 9.5 feet at 4 feet from the soil level. The bark exfoliates in a puzzle-like pattern exposing light gray, slate gray, gray-green and orangish brown colors. The bark characteristics are best shown in Sheet 3. The bark is flecked with burnt orange corkish lenticels. The exfoliation is continuous from 1" to 2" diameter upper branches to the base of the trunk. The surface roots have developed the exfoliating character.

The trunk is irregularly fluted rather than rounded which is more typical for the species.

The rich green foliage is densely borne at the ends of the fine branches creating a dense canopy. The leaf color is lighter and the texture finer than that of the species. (With the comparison being depicted in sheet 2 of the drawing) Fall color is a subdued yellow. The parent tree is growing in an 18'×18' area surrounded by concrete.

DISEASE RESISTANCE

No leaf scorch or dieback symptoms are evident even with the record droughts of the 1986–1988 years in the Athens, Ga. area. The tree is highly resistant to Dutch Elm Disease and Elm Leaf Beetle. While the tree has not been inoculation tested for resistance for Dutch Elm Disease, the tree has remained symptomless while American Elm trees in the area have been ravaged and/or killed by the disease. The tree has remained virtually free of Elm Leaf Beetle damage where less resistant (Siberian Elm) trees in the immediate area have sustained severe damage. The tree withstood −3 degrees F. without injury and laboratory tests have showed it to be hardy to −15 degrees F. It should prove hardy in USDA Zone 5b but has not been tested outdoors in those areas.

VIGOR

The mature parent tree is still relatively vigorous and typically produces 10 to 12" of terminal growth on shoots 40' above the soil surface as measured using a bucket truck. Clones of the tree in one gallon containers under standard nursery fertilization and watering practices have made 30 to 40" of new growth in a single season, reflecting that this selection has superior vigor as compared to the species.

BRANCHING AND GROWTH HABITS

This selection produces an uncommonly dense canopy due to its production of an unusually high number of twigs. Dense foliage occurs on such twigs at all exposed surfaces of the canopy, making the tree very valuable in shade production. Typical branch crotch angles average about 20 to 30 degrees to account for the distinct, strong, vase-shaped outline. While such branching would appear to predispose a tree of this type to wind, ice or snow damage, the tree has surprisingly not suffered any structural damage after occasional but repeated exposure to such conditions over the 75 to 80 years of the parent tree's life, with certain severe, occasional exposure.

TAXONOMIC CHARACTERISTICS (A) Leaves: Alternate, simple, ¾" to 2" long, ⅜" to ¾" wide, ovate to slightly obovate, lustrous bright green above (yellow-green 146B), gray-green (yellow-green 147C) beneath, acute or obtuse, oblique, simple serrate with serrations slightly more pointed than usual, glabrous above and below, 11–16 vein pairs; petiole — ⅛" to ¼" long, light green, pubescent. See sheet 2, the leaves of 'Emer II' being on the left hand side. While lighter in green hue, and slightly less lustrous than the leaves of 'Emer I', which more closely represents foliage of the species, the leaves of 'Emer II' are considered lustrous.

(B) Bud: Ovoid, imbricate, chestnut brown, slightly pubescent, ⅛" long, slightly divergent.

(C) Stem: First year: fine textured, terete, brown (grayed orange 166A), pubescent; second: gray brown, with small orangish lenticels, glabrous; pith — small, solid, brown.

(D) Fruit: Samara, oval-rounded, 10 to 12 mm long, 7 to 8 mm wide with 1 to 2 mm deep notch at distal end, light yellow green (145B), borne in axiallary cymes on 4 mm long pedicels. The flowers are inconspicuous, as in the species, and occur in early September and the fruits ripen by late October to early November in Athens, Ga.

(E) Trunk: Bark exfoliates in puzzle-like pattern exposing gray (major gray, black group 202B), slate gray (secondary grays — 202C and 201C), gray-green and orangish brown (grayed-orange 167D) colors. The bark is flecked with burnt orange (grayed orange 172B) corkish lenticels; exfoliation is continuous to the base of the trunk into the exposed surface roots. The trunk is fluted (with rounded ridges) in cross section. The unique bark qualities of this tree are seen to be outstanding and of unusual attractiveness within the species. When considered with the novel tree and trunk shapes and foliage coloration, this tree is distinctly set apart from other known Elms of the species.

(F) Propagation: Cuttings were collected on June 3, 1988 when the terminal leaf was fully mature. Cuttings were stripped of basal foliage, dipped to one inch for 5 seconds in 1.0% KIBA solution, placed in 3" by 4" cells in 2 perlite: 1 peat mix. Cuttings were then placed under intermittent mist 2½ sec/5 minutes from 8:00 a.m. to 6:00 p.m. until evaluation on July 21, 1988. "Emerald Vase" rooted 73% which is amazing considering the age of the tree. The roots penetrated through drainage holes at the bottom of the rooting container.

I claim:

1. A new and distinct variety of elm as herein described and illustrated, primarily characterized by growth habit, superb exfoliating bark, ease of vegetative propagation and resistance to leaf scorch, dieback symptoms, cold weather, Dutch Elm Disease and Elm Leaf Beetle.

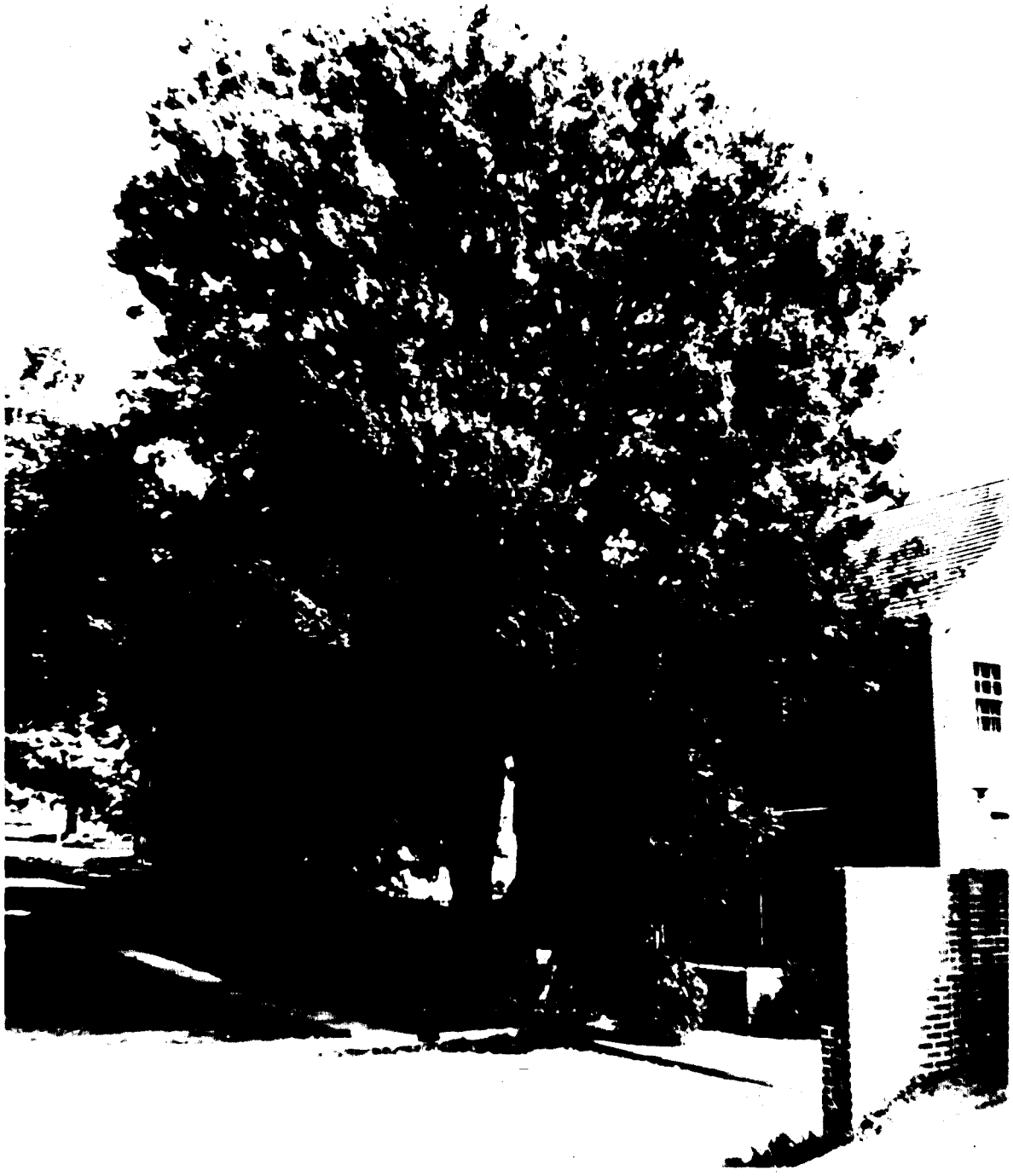

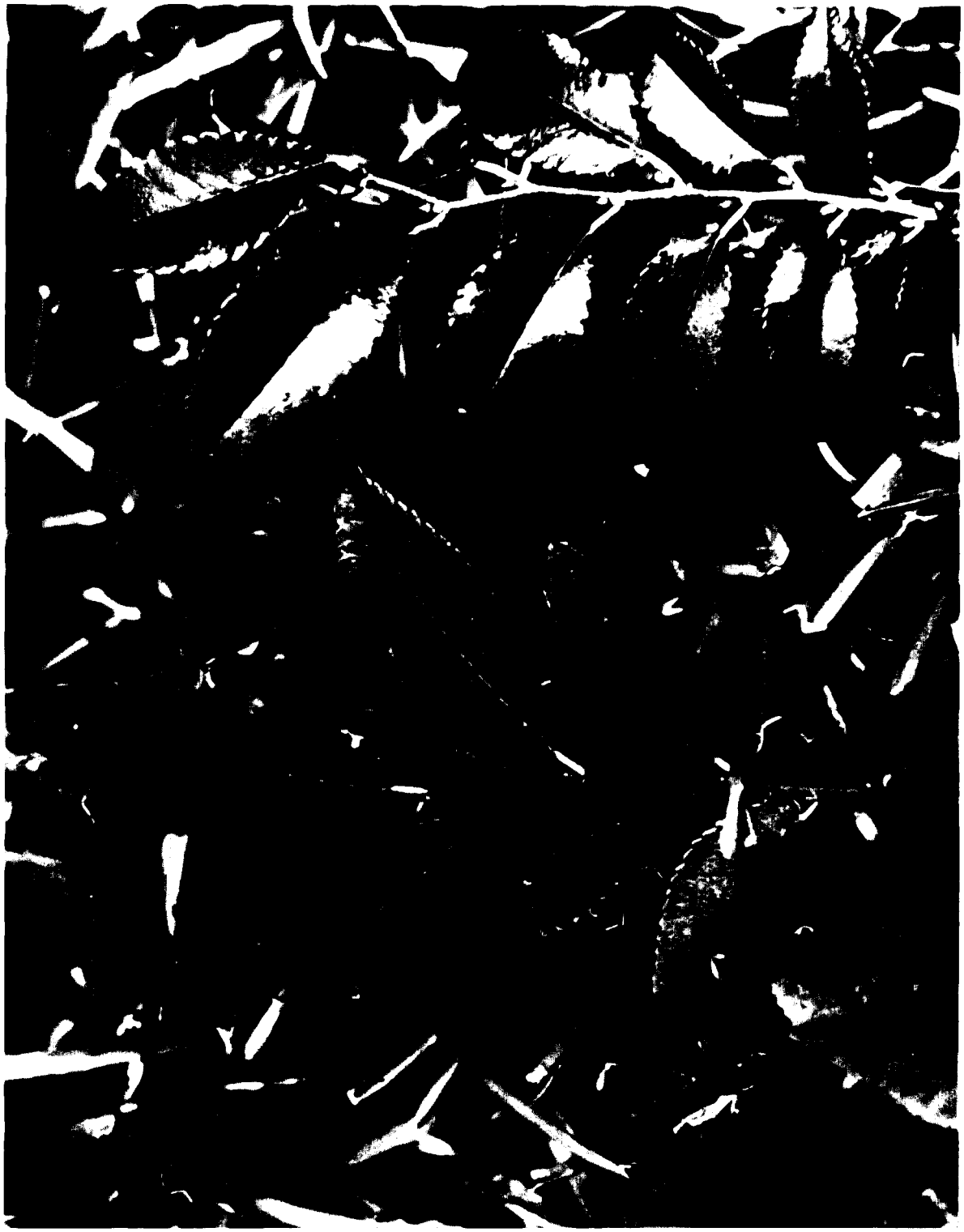

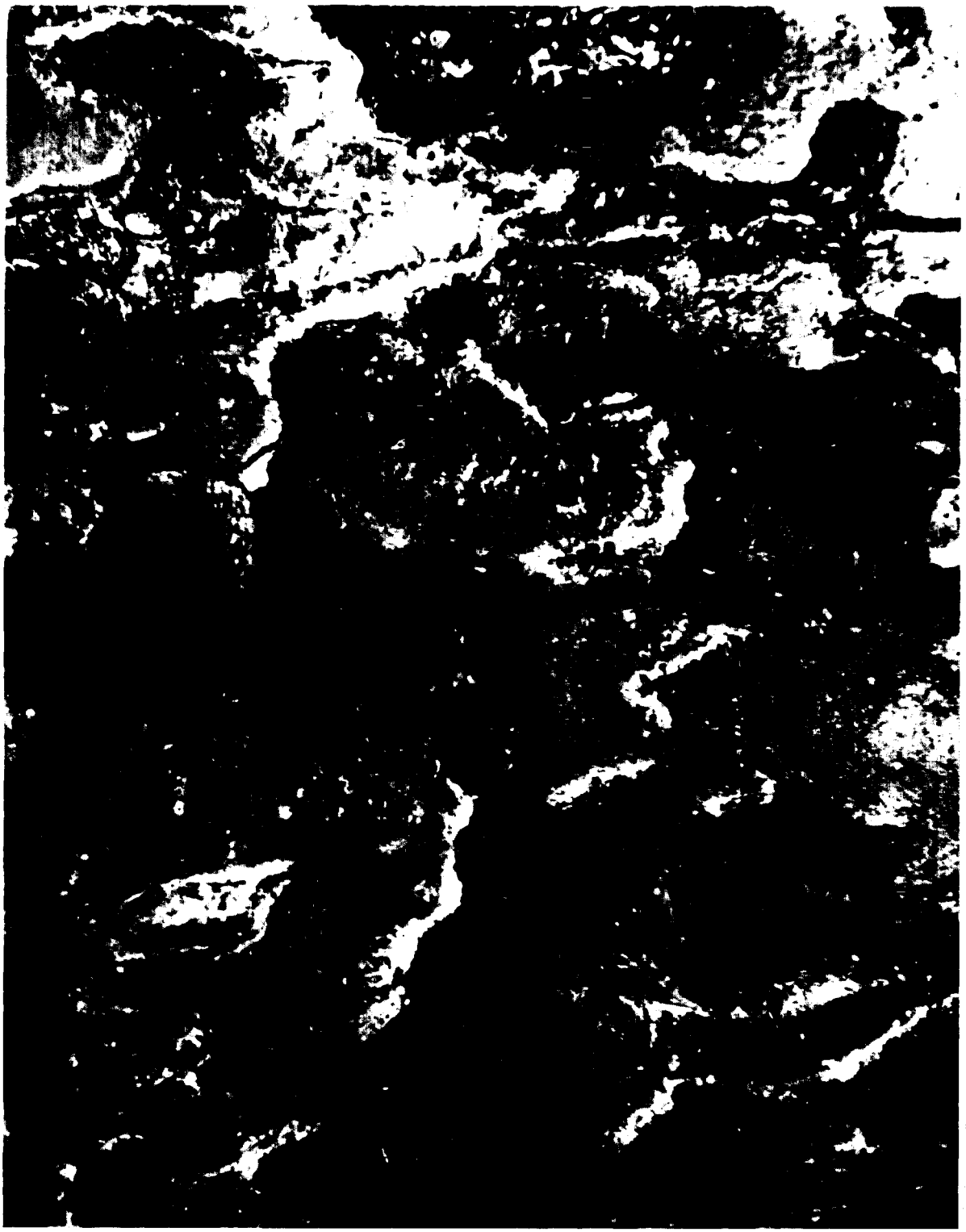

* * * * *